United States Patent [19]

Miskinyar

[11] Patent Number: 5,527,287

[45] Date of Patent: Jun. 18, 1996

[54] PRELOADED AUTOMATIC DISPOSABLE SYRINGE

[76] Inventor: Shir A. Miskinyar, 13342 Clinton St., Garden Grove, Calif. 92643

[21] Appl. No.: 447,517

[22] Filed: Dec. 7, 1989

Related U.S. Application Data

[63] Continuation-in-part of Ser. No. 208,486, Jun. 20, 1988, Pat. No. 4,894,054.

[51] Int. Cl.$^6$ .................................................. A61M 5/20
[52] U.S. Cl. .................................... 604/135; 604/156
[58] Field of Search .......................... 604/131, 135–139, 604/156–157

[56] References Cited

U.S. PATENT DOCUMENTS

| | | | |
|---|---|---|---|
| 2,017,924 | 10/1935 | Smith | 604/135 |
| 2,693,186 | 11/1954 | Riker et al. | 604/139 |
| 2,701,566 | 2/1955 | Krug | 604/156 |
| 3,066,670 | 12/1962 | Stauffer | 604/139 |
| 3,605,743 | 9/1971 | Arce | 604/157 |
| 3,797,489 | 3/1974 | Sarnoff | 604/136 |
| 4,214,584 | 7/1980 | Smirnov et al. | 604/138 X |
| 4,267,836 | 5/1981 | Whitney et al. | 604/135 |
| 4,717,383 | 1/1988 | Phillips et al. | 604/135 |

*Primary Examiner*—Corrine M. Maglione
*Attorney, Agent, or Firm*—Plante & Strauss

[57] ABSTRACT

The invention is a pre-charged, disposable syringe capable of use by patients. The syringe has a housing with a cover having a central aperture which receives an actuator button. The actuator button extends to an internal piston which is mounted over a medication ampoule. The ampoule has a dependent hypodermic needle which is slidably received in the housing and moves between recessed and projected positions. In its recessed position, the ampoule is totally contained within the housing, and in its projected position, the hypodermic needle projects from the housing. The housing contains an actuator spring, which is compressed and biased to move the piston and the ampoule into its projected position. The medication is discharged from the ampoule by the mechanically coupled piston, or by the release of air from an internal air pressure chamber. The actuator button is locked for safety with a detent and plastic ring or a trigger safety stylet and is covered with a protective, removable cap to prevent accidental or unintended injection of the medication.

20 Claims, 5 Drawing Sheets

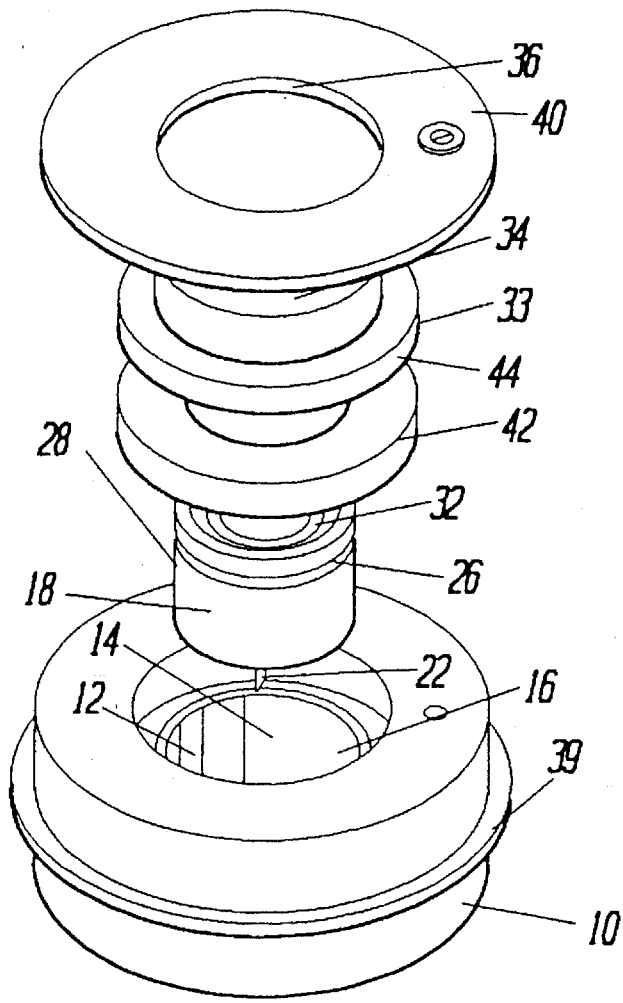
FIGURE 1
FIGURE 2
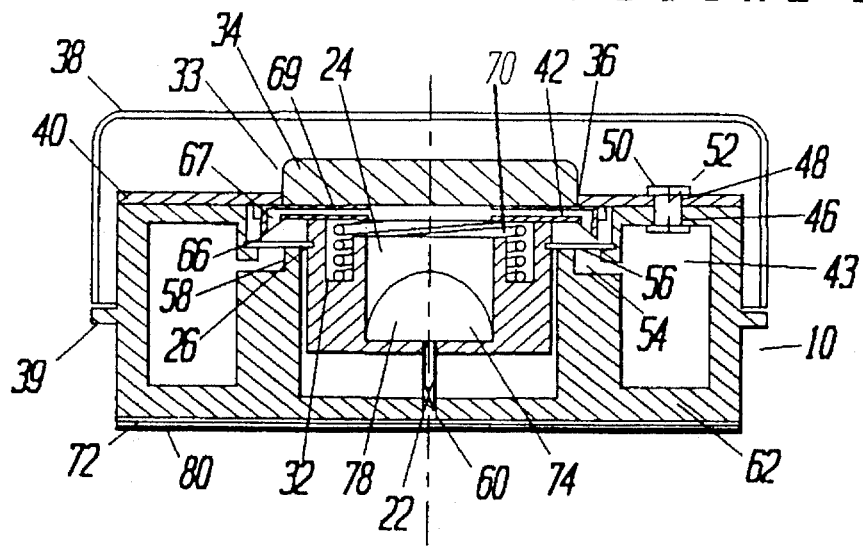

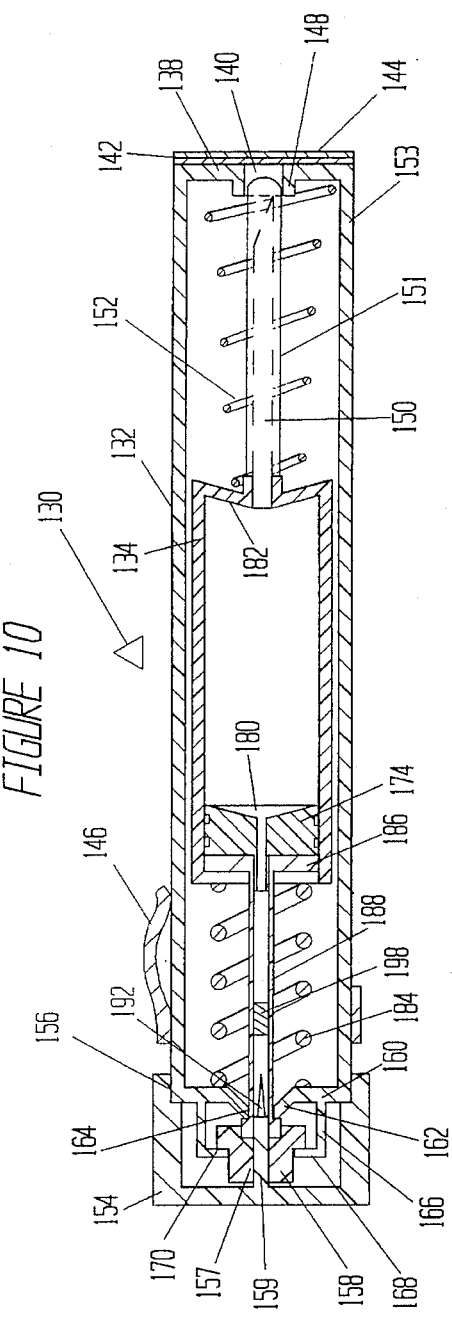
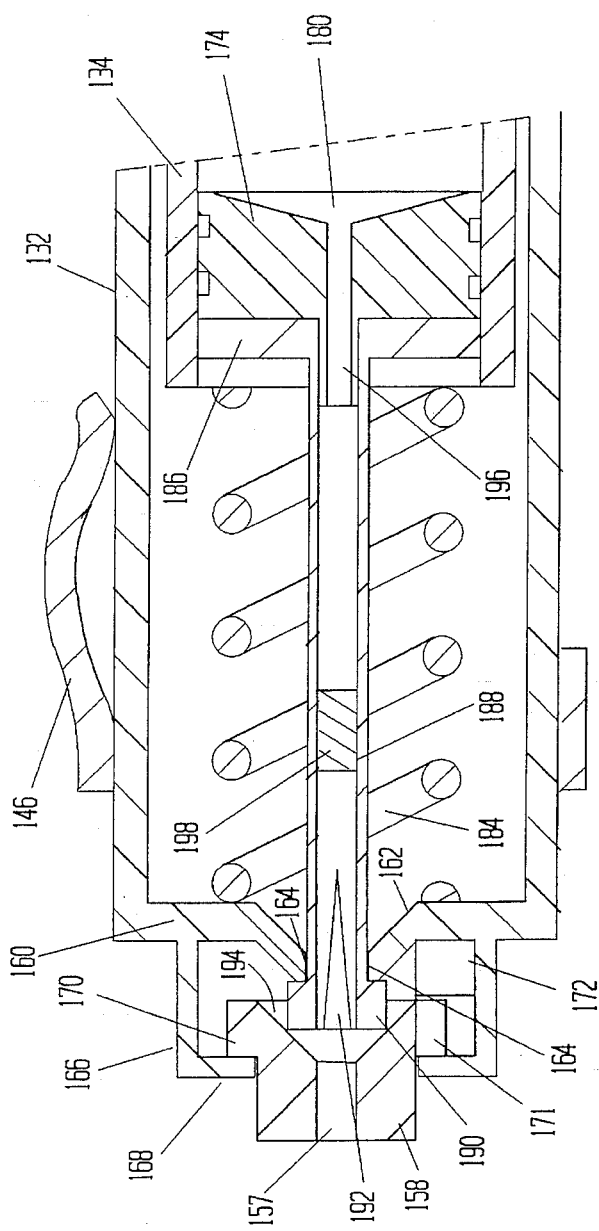
FIGURE 10
FIGURE 11

PRELOADED AUTOMATIC DISPOSABLE SYRINGE

REFERENCE TO RELATED APPLICATIONS

This application is a continuation in part of my parent application, Ser. No. 208,486, filed Jun. 20, 1988, now U.S. Pat. No. 4,894,054.

BACKGROUND OF THE INVENTION

1. Field of Invention

This invention relates to a hypodermic medicinal injector and, in particular, to a hypodermic syringe which is safe and capable of one time use by patients, handicapped, totally blind or aged persons and children.

2. Brief Statement of the Prior Art

Various devices have been marketed for automated injection of medication. A currently marketed system under the trade name Medi-Jector Easy is promoted as a needle-free, insulin injection system. While this device avoids the use of injection needles, it is intended for use by medically trained personnel to maintain proper sterility, and it is not a disposable injection system that can be readily used by patients, or incapacitated persons.

Another device which has been recently introduced is marketed under the name Inject-Ease. This device uses a hypodermic needle and has interchangeable spacer rings to control the depth of needle penetration.

None of the devices currently marketed provide a disposable needle type syringe for application of medication which is safe, sterile and is adaptable for use by patients, including children and handicapped and elderly patients. In many applications, there is no current substitute for administration of medication by medically trained and skilled persons, since there is no syringe which heretofore has been available with accurately measured dosages of medication, and which can be used by the patient. Thus, diabetic patients, or patients suffering chronic allergies, must be dependent upon receiving medical attention and care for administration of medication.

A syringe for use by patients must be disposable, with a design which will prevent reloading, thereby avoiding misuse of the syringe and the possibility of cross infection with agents such as AIDS viruses. The hypodermic needle of the syringe should be totally protected from contamination, and the syringe should be capable of mass production, thereby insuring its low cost. It is a desirable objective, at this time, to supply the syringe with variable size needles from ⅛ to ¼ inch and of 23 to 30 gauge, for pediatric, adults and obese patients. It is also an objective to provide a syringe which is preloaded by a licensed pharmaceutical company, insuring sterility and accuracy of dosage and strength of the medication.

BRIEF STATEMENT OF THE INVENTION

This invention comprises a pre-charged, disposable syringe capable of use by patients. The syringe includes a housing with a cover having a central aperture which receives an actuator button. The actuator button extends to an internal piston which is mounted over a medication ampoule. The ampoule has a dependent hypodermic needle which is slidably received in the housing for movement between recessed and projected positions. In its recessed position, the ampoule is totally contained and supported within the housing, and in its projected position, the hypodermic needle projects out of the housing. The housing contains an actuator spring, which is compressed and biased to move the piston and the ampoule into its projected position. The medication is discharged from the ampoule by the mechanically coupled piston, or by the release of air from an internal air pressure chamber. The actuator button is locked for safety with a detent and plastic ring, latch, or trigger, and is covered with a protective, removable cap to prevent accidental or unintended injection of the medication.

BRIEF DESCRIPTION OF THE DRAWINGS

The invention will be described with reference to the figures of which:

FIG. 1 is an exploded perspective view of the air activated embodiment of the invention;

FIG. 2 is an elevational sectional view of the embodiment of FIG. 1, fully loaded in a static, preactivated state;

FIG. 10 is a sectional view of an alternative syringe in its loaded configuration;

FIG. 11 is an enlarged view of the trigger end of the syringe of FIG. 10, with the cover removed;

DESCRIPTION OF PREFERRED EMBODIMENTS

Figure 3:
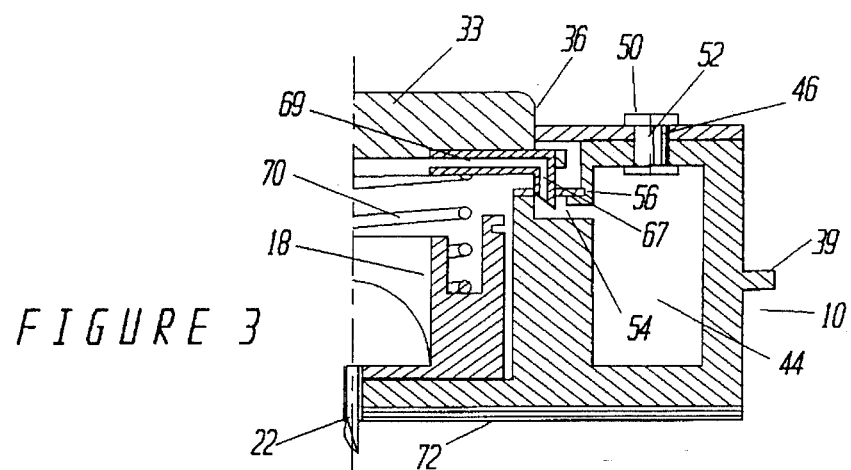
FIG. 3 is a partial, elevational sectional view of the embodiment of FIG. 1 is its discharged state.

Referring now to FIG. 1, the invention is illustrated in exploded view. The particular embodiment illustrated in FIG. 1 is the air activated device. The device has a housing 10 which is preferably cylindrical of relatively low height or elevation, and has a central cavity 12 which receives the operating mechanism. The central cavity 12 has an internal well 14 with a right-angle, vertical cylindrical wall 16 which slidably receives a cylindrically shaped ampoule member 18. The ampoule member 18 has a hypodermic needle 22 that extends through its under surface and communicates with the medication chamber, described in greater detail with reference to FIG. 2. An annular groove 26 is provided about the outer side wall 28 of the ampoule 18 which is engaged by a sealing plastic ring (shown in FIG. 2). The upper end of the sidewall of the ampoule 18 has an annular recess 32 which serves as a chamber for housing a compression spring (also shown in FIG. 2). The actuator button 33 has a central upright boss 34 which is received in the central aperture 36 of the cover 40. The button 33 and has a circular base 44 which carries, on its undersurface, a knife 42 having a circular blade.

Referring now to FIG. 2, the invention will be described in greater detail. As shown in FIG. 2, the housing 10 has an outer annular chamber 43 which is the air supply chamber for the mechanism. A fill port 46 is provided in the upper wall of the air chamber and this port 46 communicates with an aligned aperture 48 in the cover. A pneumatic valve 50 is inserted in the aligned aperture 48 and fill port 46. This valve 50 is of a general grommet-shape with a through passage 52 that is normally sealed by the resilient deformation of the valve member under the internal pressure within the air chamber. The internal air chamber communicates with the interior, medication chamber 24 through a valve 54 which is sealed by a plastic ring 56. The valve has an annular seat 58 and is entirely covered by this plastic ring seal 56. The seal 56 is received in annular groove 26 about the ampoule member 18, and thus also serves as a detent to restrain the ampoule member 18 and needle 22 within the housing. Seated within the medication chamber 24 is the cylindrical cup-shaped ampoule member 18 which supports the hypodermic needle 22 on its under surface. The hypodermic needle 22 is aligned with a central through aperture 60 in the bottom wall 62 of the housing 10 and is of sufficient length that when the ampoule member 18 is in its illustrated, retracted position, the hypodermic needle 22 is withdrawn from this aperture 60. The ampoule member 18 has sufficient travel within the housing 10 to project the needle 22 through the aperture 60 and a predetermined distance into the tissue of the patient.

The actuator button 33 has a central raised boss 34 that extends through the central aperture 36 of the cover 40. The button 33 is enclosed within a protective cover 38 which seats against an annular rim 39 about the mid-portion of the housing 10. The cover 38 can be sealed to the housing by a tear tape, if desired. The button 33 supports, on its undersurface, a knife 42 with a circular blade. The knife blade has a sharp circular cutting edge 66 which is aligned with the plastic ring 56 so that it will puncture this plastic ring and permit the discharge of the pressured air from the annular air chamber 43 past the valve and into the ampoule chamber. The knife also has a circular groove 67 which communicates with a passageway 69 that extends into communication with the internal chamber 24 of the ampoule member 18.

The ampoule member 18 has an annular well 32 in its upper edge which provides a chamber for the actuator spring 70. The actuator spring 70 is a compression coil spring biased between the undersurface of the button 33 and the bottom wall of the annular well 32. This spring has sufficient strength and resiliency to advance the ampoule member 18 instantaneously upon release of the detent, previously described, and extend the hypodermic needle 22 through the frangible sterile tape 72 on the undersurface of the housing and into the patient's subcutaneous space. The extended positions of the ampoule member 18 and needle 22 are shown in FIG. 3. This extension of the ampoule member 18 and hypodermic needle 22 occurs sufficiently rapidly to precede the application of air pressure through circular groove 67 in the knife 42 and the passageway 69 of the button. Thus the needle 22 is extended before air pressure is applied to the ampoule 74 contained within the ampoule chamber 24. The ampoule 74 is formed by an elastic balloon which is received within and sealed to the inner walls of the ampoule chamber, containing medication 78 within its sealed interior. The air pressure supplied by the air chamber 43 through the air valve 54 and into the ampoule chamber is sufficient to collapse the medication balloon and inject the medication 78 contained within the balloon into the patient.

The undersurface of the housing 10 has a frangible sterile tape 72 which is permanently bonded to the housing, and which overlies the through aperture 60, and an overlying, protective sterile tape 80. The protective overlay tape 80 is bonded to the housing and the sterile tape 72 with a pressure sensitive adhesive to permit its removal from the injection device immediately prior to use.

Figure 4:
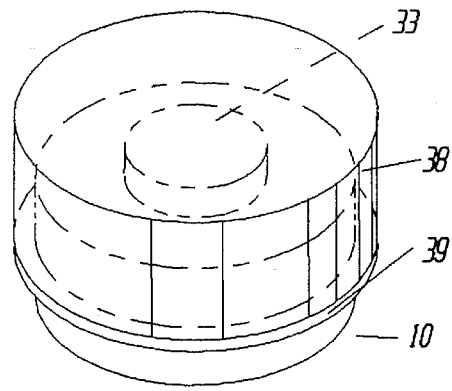
FIG. 4 is a perspective view of the assembled and loaded syringe of the invention.
Figure 5:
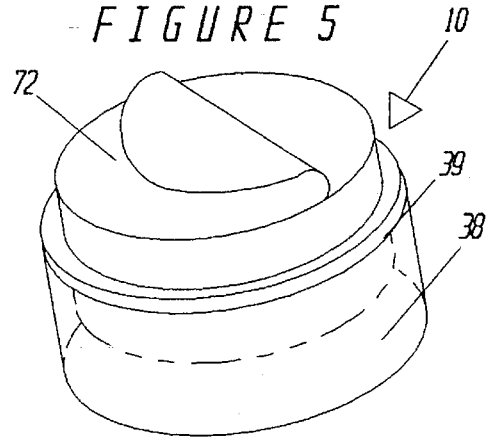
FIG. 5 illustrates removal of the protective tape from the underside of the syringe.
Figure 6:
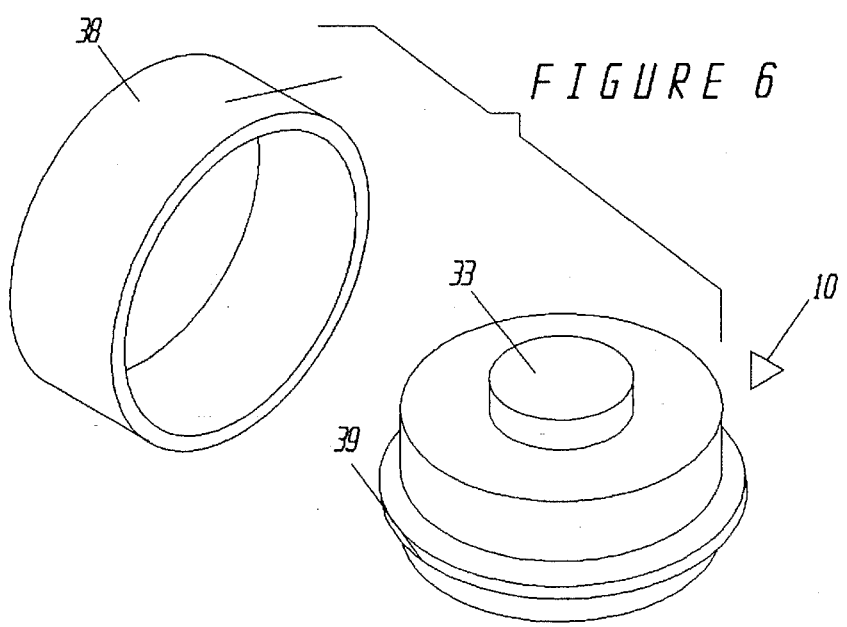
FIG. 6 is a view of the syringe, uncovered, and in a position to inject its medication.
Figure 7:
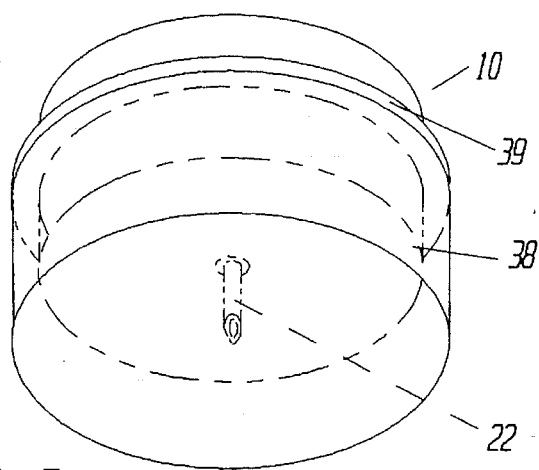
FIG. 7 is a view of the syringe after use, with the cover replaced on its undersurface for disposal.

FIG. 4 illustrates the hypodermic syringe of the invention as it would be received by the patient. The syringe is preloaded with a precisely measured dosage of medication and has the proper selection of needle size for the patient. All of this information can be coded on the syringe itself. The protective cover 38 overlies the actuator button 33, and must be removed by the patient for access to the button. As shown in FIG. 5, the patient or user will first remove the protective overlay tape 80, exposing the underlying frangible, sterile tape. As shown in FIG. 6, the patient will then position the syringe against a suitable skin surface. Preferably, the undersurface of the housing and the sterile tape 72 is coated with an antiseptic pressure sensitive adhesive so that, when placed on the skin of a patient, the undersurface of the device will disinfect and be slightly tacky and will stick to the skin of the patient. The patient then depresses the actuator button 33, breaking the detent of the plastic ring 56. As will be described hereinafter, other detents can be used, such as a latch mechanism (see FIGS. 12 & 13), of a trigger (see FIGS. 10 & 11). The breaking of the plastic ring 56 will release the spring 70 to advance the knife 42 through the plastic ring 56, and permit the ampoule member 18 to be ejected into its extended position. The air pressure which is also released from the annular air chamber 43 will fill the ampoule chamber 24, raising its internal pressure sufficiently to eject the medication from the ampoule 74. Once the injection is completed, the patient removes the device which is disposed as it cannot be readily reloaded for reuse. For this purpose, the protective cover 38, which was removed from over the actuator button, is replaced on the underside of the syringe, totally enclosing the needle 22, as shown in FIG. 7.

Figure 8:
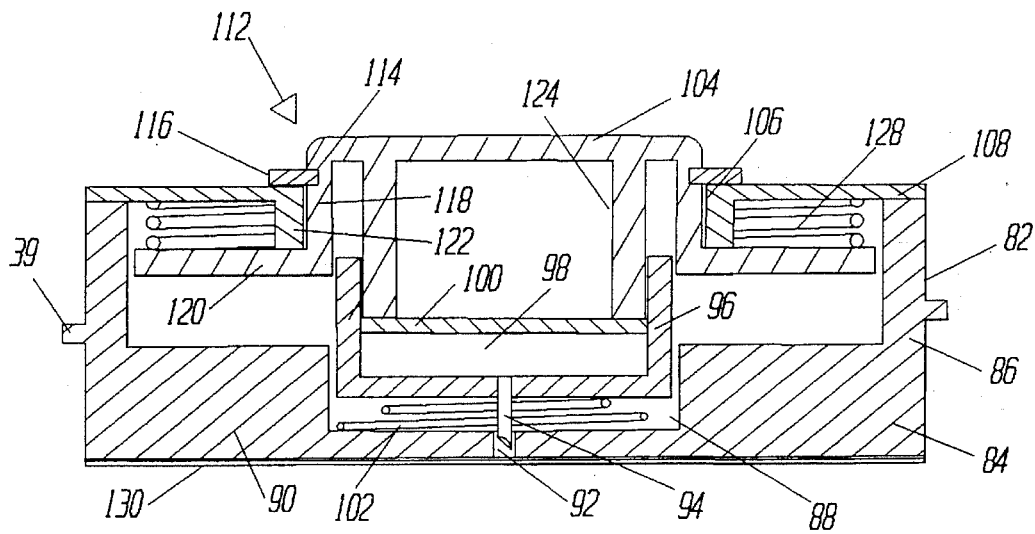
FIG. 8 is an elevational sectional view of a spring activated mechanism, in a static, preactivated state.

Referring now to FIG. 8, the alternative embodiment of the invention will be described. As there illustrated, this device 82 has a cylindrical, cup-shaped housing 84 having an outer wall 86 defined by a right-angle cylindrical wall, and a central lesser diameter well 88. The bottom wall 90 of the housing 84 has a central through aperture 92 which slidably receives the hypodermic needle 94. The ampoule member 96 is a cylindrical cup-shaped member which contains medication 98 and which also receives a slidable piston 100. The piston 100 engages the inside wall of the cylindrical member 96 in a sliding seal which prevents leaking of the medication from the ampoule member 96. The ampoule member 96 is resiliently biased into its retractable position by a helical coil spring 102 which is seated in the central well 88 of the housing and which is collapsed when the ampoule member 96 is driven into its extended position.

The actuator button 104 is slidably received in a central aperture 106 of the top cover 108. The actuator button 104 is restrained to this cover by a detent 112 formed by an annular groove 114 about its outer, upper wall in which is seated a resilient clip washer 116. The button 104 has a cylindrical skirt 118 and a single, outwardly flared flange 120. The cover 108 has a central inwardly and downwardly dependent skirt 122 which receives the cylindrical skirt 118 of the actuator button 104.

A cylindrical boss 124 is downwardly dependent from the undersurface of the button 104 and has a diameter to permit it to be received within the ampoule member 96. The boss 124 is immediately above, and attached to, the piston 100 which is slidably contained within the ampoule member 96. An actuator spring 128 in the form of a compression coil spring is resiliently biased between the undersurface of the cover and the upper surface of the flange of the actuator button. When the device is in its armed and loaded condition as illustrated in FIG. 8, the actuator spring 128 is compressed.

Figure 9:
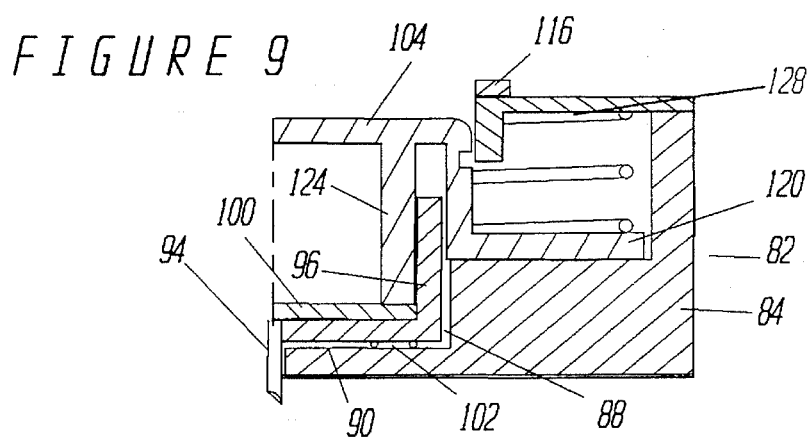
FIG. 9 is an elevational sectional view of the device of FIG. 8 is its discharged state.

In use, the patient removes the protective overlay tape 130 from the undersurface of the device, in the manner previously described and illustrated in FIG. 5. Preferably, the undersurface of the device has an antiseptic, pressure sensitive coating permitting its application to the skin of a patient. In this position, the device is ready for injection of the medication which is contained within the ampoule member 96. The patient presses on the actuator button 104 sufficiently to override the resilient detent of the circular clip washer 116. This permits the actuator spring 128 to be released, forcing the ampoule chamber 96 outwardly into its extended position, which is shown in FIG. 9. In this position, the ampoule needle 94 projects through the central opening of the bottom plate and injects into the patient's skin. When the ampoule chamber 96 bottoms against the bottom wall 90 of the central well 88, the actuator spring 128 continues the travel of the actuator button, and advances the piston 100 through the ampoule chamber 96, injecting the medication 98 in this chamber through the hypodermic needle 94, into the patient. The resilient bias of the retraction spring 102 is designed to be less than the force required for slidably advancing the piston 100 in the ampoule chamber 96, thereby ensuring that the medication is not prematurely ejected from the ampoule chamber.

Referring now to FIG. 10, there is illustrated another embodiment of the invention. In this embodiment, the syringe 130 is provided with a long housing 132, more typical of syringes. The syringe has a syringe ampoule 134 that is slidably received within its external housing 132. The housing 132 and ampoule 134 of the syringe 130 are cylindrical and the housing 132 has with a bottom wall 138 having a central opening 140 which is covered with a sealing membrane 142 and, preferably with a protective overlay 144 which is removed prior to use. The housing 132 can have an external clip 146 formed of plastic or metal to permit securing the syringe in a pocket of a shirt or gown.

The interior surface of the bottom wall 138 supports a cylindrical well 148 that permits passage of the needle 150 of the syringe, and centers the helical spring 152 which biases the ampoule of the syringe into its illustrated, retracted position. The needle 150 can be protected with a covering or sheath 151 which is punctured when the needle is ejected.

At its upper end, the housing 132 supports a removable cap 154 which has an annular groove 156 in its lower edge to receive the upper end of the housing 132. The syringe 130 of this embodiment uses a trigger release, which has an activation button 158. The cap 154 overlies and contains the activation button 158.

As shown in both FIGS. 10 and 11, the upper end of the housing has a top wall 160 which supports a fustro-conical boss 162 with a central opening 164 that is entirely surrounded by a cylindrical wall 166. The upper end of the cylindrical wall 166 has an inwardly directed annular lip 168 which serves to retain the larger diameter base 170 of the activation button 158. As shown in FIG. 11, the annular base 170 of the button 158 is discontinuous with axial ridges 171, and the sidewall of the cylindrical wall 166 can have axial grooves 172 to receive the ridges 171 only when the button 158 is rotated to align the ridges 171 with the axial grooves 172, thereby requiring that the button 158 be rotated into an indexing position with the housing before it can be depressed.

The ampoule 134 slidably receives a piston 174 which seals against the sidewall of the ampoule cylinder. The undersurface of the piston 174 has a conical recess 180, and preferably this has the same conical angle as the dished lower wall 182 of the ampule 134. A compression actuator spring 184 is mounted in the upper end of the housing. A flange 186 supports a retainer sleeve 188, and rests on the upper surface of piston 174. The spring surrounds sleeve 188, and is captured between the upper end of the housing and the flange 186, which bears directly against the upper end of piston 174. The retainer sleeve 188 is received through the central opening 164 in the boss 162 of the upper end wall of the housing, and has an outer annular rim 190 (see FIG. 11) which is captured by the end of the boss 162. The sleeve 188 has at least one, and preferably, two slots 192 in its upper end, to permit inward deflection of its sidewalls a sufficient distance to permit passage of the rim 190 through the opening 164 in the boss 162.

The actuator button 158 is confined beneath the lip 168 of the cylindrical wall, and has a conical recess 194 (see FIGURE) which receives the upper end of the sleeve 188. The conical recess 194 provides the necessary inwardly directed radial force component to deflect the ends of the sleeve 188 sufficiently to permit rim 190 to clear the opening in the end wall of boss 162.

The actuator button 158 also has a central aperture 157 which receives a stylet 159 (see FIG. 10) which is supported on the undersurface of cap 154. This stylet serves as a safety lock since it enters the end of retainer sleeve 188 and prevents deflection of its sidewalls, thereby insuring that when the cap 154 is in place, the syringe cannot be inadvertently actuated.

When released through the opening, the sleeve 188 and flange 186, together with the ampoule 134 are driven into an extended position with needle 150 projecting through sealing membrance 142 and sheath 151, and penetrating the patient's skin. Continued extension of the activation spring 184 moves piston 174 downwardly, discharging the contents of the ampoule 134 through needle 150. After the syringe is removed, the cap 154 can be placed over the lower end of the housing, covering the needle 150 for disposal of the syringe. As shown in FIG. 10, a sleeve 153 can also be placed over the end of the syringe, and this sleeve can be slid down to cover the needle after use.

The ampoule 134 is filled with medication through the sleeve 188. For this purpose, the piston 174 has a central opening, preferably with a neck 196 which extends into the sleeve 188. The ampoule is filled in a vertical position so the conical recess 180 serves as a bubble collector, insuring complete elimination of any air bubbles. Once filled, the ampoule is sealed by inserting a plug 198 into the sleeve, which can be retained by friction fit, or, alternatively, with a heat seal, or ultrasonic bonding. The medication can be placed in the ampoule in a sterile room, and the plug 198 is inserted and the needle is covered with sheath 151. Thereafter the remaining assembly of the syringe can be conducted outside of the sterile room, since there is no opportunity for contamination of the medication.

The needle 150 of the ampoule has a limited length, e.g., from about 2 to 8 millimeters for subcutaneous injections and from 0.75 to 1.5 inch for intramuscular injections. These lengths are insufficient for intravenous injections, thereby insuring against misuse of the syringe.

Figure 13:
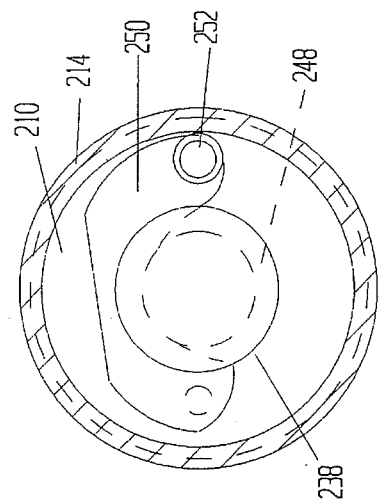
FIG. 13 is a sectional view along line 13—13' of FIG. 12.
Figure 14:
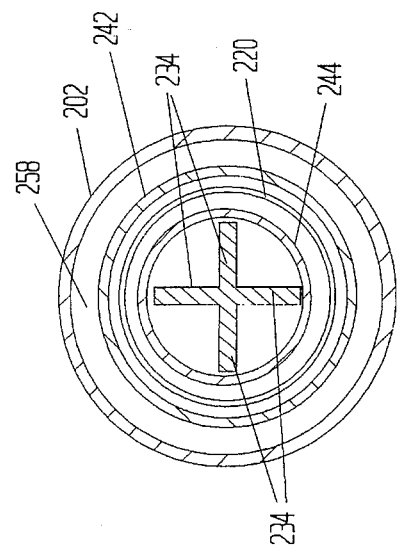
FIG. 14 is a sectional view along line 14—14' of FIG. 12.
Figure 12:
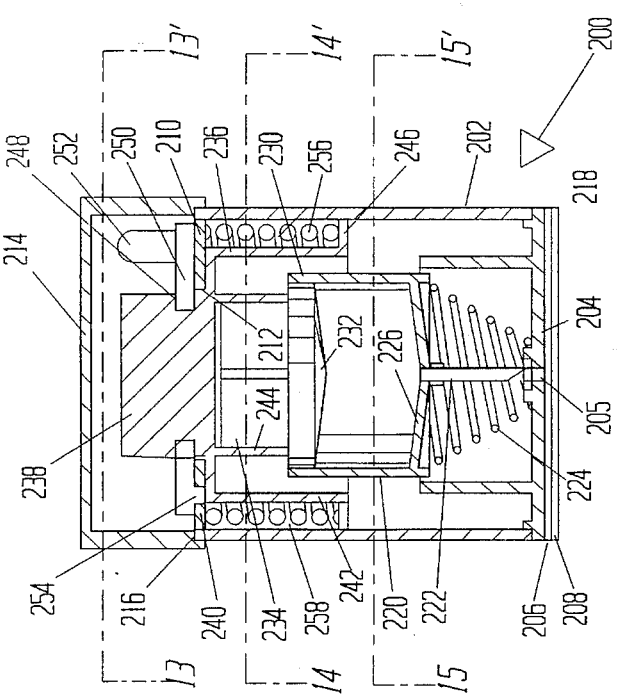
FIG. 12 is a view of an alternative embodiment.
Figure 15:
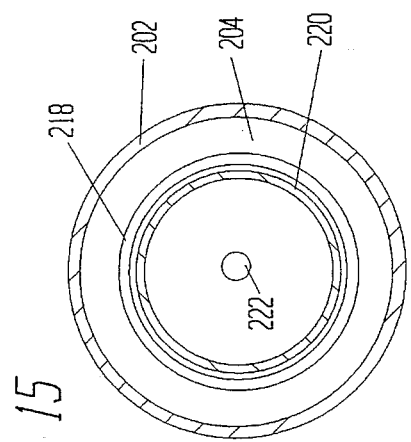
FIG. 15 is a sectional view along line 15—15' of FIG. 12.

Referring now to FIGS. 12 through 14, another embodiment of the syringe is shown. In this embodiment, the syringe 200 has a latch mechanism for release of the ampoule. As previously mentioned, however, any of the illustrated syringes can be provided with the detent (such as shown in FIG. 8, the trigger release (such as shown in FIG. 10) or the latch, which is illustrated in FIGS. 12–14. The syringe 200 has an outer cylindrical housing 202 which has a permanently attached bottom wall 204 with a central opening 205 that is covered with a sealing membrane 206 and a protective overlay 208. At its opposite end, the housing has a permanently attached top wall 210 with a central opening 212, and is covered with a protective cap 214, which has an annular shoulder 216 to seat on the end of the housing.

The bottom wall 204 has an integral cylindrical sleeve 218, forming a well which slidably receives the ampoule 220. The needle 222 of the syringe 200 is supported by the bottom wall of the ampoule 220, aligned with the opening 205 in the bottom wall 204 of the housing. A helical compression spring 224 is mounted within the well, biased between the bottom of the ampoule 220 and the bottom wall 204, thereby serving as a retractor spring to maintain the ampoule 220 in a retracted position. The bottom wall 226 of the ampoule 220 is conical, thereby forming an annular bottom shoulder 228 which retains the helical spring.

A piston 230 is slidably received in the ampoule 220 with a sliding seal against the inside wall of the ampoule. Preferably the bottom 232 of the piston is conical with the same angle as the conical bottom wall 226 of the ampoule 220 to insure complete discharge of all medication within the ampoule. The conical bottom wall 226 of the ampoule also serves as an air bubble collector during filling of the ampoule.

The upper end of the piston supports four vertical flanges 234 which lie on radials, forming a cross (see FIG. 14). An actuator carriage 236 is slidably received within the housing, and this carriage 236 has a central cylindrical boss 238 with a circular flange 240 with an outer skirt 242, and an inner, concentric skirt 244. The outer skirt 242 has an integral, outwardly directed annular lip 246.

The boss 238 of the carriage 236 is received through the central opening 212 of the top wall 210. An annular groove 248 is formed in the boss 238, and this groove 248 receives a latch arm 250 (see FIG. 13). The latch arm 250 has an actuator knob 252 and is pivotally supported on top wall 210 by a protuberance 254 which seats in a recess in the top wall 210. After the cap 214 is removed, the latch arm 250 can be pivoted away from the boss 238, releasing the carriage 236.

The carriage 236 is biased towards the bottom wall 204 of the housing by actuator compression spring 256. The spring 256 is contained in the annulus 258 formed between the outer skirt 242 and the inside wall of the housing, captured between annular lip 246 and the top wall 210.

When the cap is removed, and the latch arm is pivoted away from the boss, the carriage is released to drive the ampoule towards the bottom of the housing, and to project the needle out of the housing. The needle penetrates the user's skin and the continued movement of the carriage will inject the medication from the ampoule into the patient.

Special Advantages of the Invention

The ejection operation of the invention is smooth and continuous with the initial advance of the ampoule chamber and hypodermic needle which eject with sufficient force for the needle to penetrate the skin of the patient. This initial movement is immediately followed by the continuous injection of the medication contained within the ampoule chamber.

Since the device of this invention cannot be readily reloaded it is safe for prescription as a disposable, single use medication. The device is very safe for use by patients and since it can only be used once, there is no possibility of passing a contagious or infectious diseases such as AIDS or other HIV viruses. The device can be provided with variable capacity and with needles of varied sizes and lengths suitable for pediatric use, or use by adults or obese persons.

Since the device can be readily used by the patient, it is ideally suited for diabetic control, for anaphylatic shock, such as encountered with allergic or hypersensitive individuals, e.g., for dispensing of medication for bites by snakes, bees, insects, etc., and for inoculation with various vaccines. As the device is entirely pre-loaded, little physical ability and judgement is required of the patient and the device can be used by children, handicapped persons or persons whose judgement or dexterity has been temporarily impaired by shock, and other undesired occurances.

The device can be used to inject only vertically as it has a large exterior surface that is applied to the skin which is relatively large and which stabilizes the fast penetration of the needle. Accordingly the device cannot be used for intravenous injections as its instanteous needle penetration and injection is incompatible with the intravenous injection which requires skilled and licensed personnel with slow, steady needle penetration.

Preferably, the device is provided with a transparent structure, e.g., formed of transparent plastics, thereby readily permitting observation of the contents of the ampoule. The actuator button can be suitably color-coated, e.g., preferably molded of a red colored plastic. In its preferred embodiment, as shown in FIG. 3, the device also includes a protective cover 132 which is mounted about the side wall 134 of the housing 84 and which engages against an annular rim 136 that extends about the periphery of the housing, preferably at its mid-portion. This permits the cover to be reapplied over the opposite end of the housing after use, thereby encasing the needle in a protective chamber when the device is disposed.

The extreme compactness of the device and its low profile stabilizes the device when used by the patient. Additionally, the low profile and compactness of the injection device greatly aids packaging and distribution by the pharmaceutical supply house.

All of the component parts of the injection device can be fabricated of readily available materials such as plastics using injection molding techniques for mass production. The device can be marketed with significantly lower costs than conventional automatic syringes. The device can be assembled and pre-loaded with measured amounts of medication under sterile conditions by the pharmaceutical supply house and can be sealed with the frangible sterile tape and the protective overlay tape, isolating the medication from contact with the external environment.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. An automatic syringe comprising:
   a. a one-piece body with a cylindrical inside wall and having an injection end and an actuator end;
   b. an injection end wall permanently secured to said injection end of said body and having a cylindrical well on its inside surface which extends coaxially within said body forming an open interior annulus within said body;
   c. a medication-containing ampoule bearing an injection needle and slidably received within said well;
   d. a piston slidably received within said ampoule;
   e. a actuator end wall having a through aperture and permanently secured to the actuator end of said body;
   f. an actuator carriage having an inner end received against said piston and having its opposite end extending through said aperture and exteriorly of said body, and having an annular flange with a downwardly dependent integral cylindrical skirt with an annular lip extending radially outwardly and bearing against the inside wall of said body and slidably received within said annulus; and
   a compression spring captured between said annular flange and said actuator end wall.

2. The syringe of claim 1 wherein said injection end wall and cylindrical well are a one-piece member.

3. The automatic syringe of claim 1 wherein said actuator carriage has a cylindrical skirt extending coaxially within said cylindrical inside wall, and wherein said annular flange extends radially outwardly from the end of said skirt.

4. The automatic syringe of claim 3 wherein said actuator carriage, annular skirt and annular flange are a one-piece member.

5. In an automatic syringe in which an ampoule having a medication-containing chamber with
   a. a hypodermic needle in open communication therewith is slidably received within an outer housing having an actuator end wall and an opposite, medication injection end wall, a needle passage in said medication injection end wall, a membrane seal on said injection end wall covering said needle passage, with said chamber being moveable between a fully retracted position and an extended position wherein said needle projects through said needle passage of said housing a sufficient distance for subcutaneous injections, and is biased by an actuator spring into its extended position, which spring is retained in a compressed state by a detent having a detent release member supported at said actuator end wall externally of said housing, and wherein said ampoule contains a slidably received piston to effect discharge of its contents, the improvement comprising:
   b. an inner cylindrical wall, integral with, and in the interior of, said housing extending from said medication injection end wall and slidably receiving said ampoule and being of a lesser diameter than said housing to form a first annulus with the outer wall of said housing;
   c. an aperture in said actuator end wall;
   d. a one-piece actuator carriage having a central boss with its upper end extending through said aperture in said actuator end wall, exteriorly of said housing with said boss bearing an integral detent element cooperative with said detent releasing member, and at least one integral projection on its lower end which bears directly against said piston and an integral circular flange axially located between said boss and said projection with a downwardly dependent, integral cylindrical skirt having a diameter permitting its slidable reception within said first annulus and forming a second annulus with the wall of said housing, said skirt also having at its lower end an integral annular lip extending radially outwardly into contact with the inner wall of said housing; and
   e. said actuator spring being received within said second annulus and biased between said actuator end wall of said housing and said lip.

6. The automatic syringe of claim 5 wherein said piston has a conical face on its undersurface.

7. The automatic syringe of claim 6 wherein the end of said ampoule opposite said piston has a conical inner end wall having a contour mating with the conical face of said piston.

8. The automatic syringe of claim 1 including a medication within said medication chamber of said ampoule.

9. The syringe of claim 5 including a helical compression spring which is received within said inner cylindrical wall, between said ampoule and the inside medication end wall of said housing.

10. The automatic syringe of claim 1 including a cup-shaped cap received over the actuator end of said housing to enclose said detent release member.

11. The syringe of claim 10 wherein said cap can be placed on the injection end of said housing to totally enclose said needle in its extended position.

12. The syringe of claim 5 wherein said integral detent element comprises at least one groove in said upper end of said boss of said actuator driver which receives said detent.

13. An automatic syringe which comprises:
   a. a syringe body having an outer wall and a medication injection end wall, a needle passage in said medication injection end wall, and a membrane seal on said injection end wall covering said needle passage;
   b. a medication-containing retractable ampoule with a needle, said ampoule slidably received within said syringe body;
   c. an ejection mechanism within said syringe body and having a detent located and operable externally of said body to release said mechanism and advance said ampoule and needle and project said needle exteriorly of said body; and
   d. a protective sheet material overlying said membrane seal and bonded thereto by a peelable, pressure sensitive adhesive.

14. The automatic syringe of claim 13 wherein said pressure sensitive adhesive includes an antiseptic agent.

15. The syringe of claim 14 wherein said pressure sensitive adhesive includes a tacifier agent, rendering the underside of said syringe tacky upon removal of said protective sheet material.

16. The automatic syringe of claim 13 including a piston which is slidably received within said ampoule to effect discharge of its contents.

17. The automatic syringe of claim 16 including an inner cylindrical wall extending within said body from said medication injection end wall and slidably receiving said ampoule and being of a lesser diameter than said body to form a first annulus with said outer wall of said body.

18. The automatic syringe of claim 17 wherein said ejection mechanism includes a one-piece actuator carriage having a centrally positioned, integral projection bearing directly against said piston and a circular flange integral with said carriage with a downwardly dependent, integral cylindrical skirt having a diameter permitting its slidable reception within said first annulus and forming a second annulus with said outer wall of said housing, said skirt also having at its lower end an annular lip extending radially outwardly to said outer wall of said housing.

19. The automatic syringe of claim 18 wherein said ejection mechanism includes an actuator spring captured within said second annulus, which spring is retained in a compressed state by said detent.

20. An automatic syringe which comprises:

a. a syringe body having an actuator end wall with an aperture;

b. a medication-containing retractable ampoule with a needle, said ampoule slidably received within said syringe body;

c. an ejection mechanism within said syringe body to advance said ampoule and needle and project said needle exteriorly of said body including a piston slidably received within said body and having an upper end extending through said aperture, a groove in said upper end; and d. a detent comprising a lever arm which is pivotally mounted on a longitudinally axially disposed axis on the outside of said actuator end wall and is moveable between a detenting position seated in said groove and a releasing position removed from said groove.

* * * * *